US012478729B2

(12) United States Patent
Kim et al.

(10) Patent No.: US 12,478,729 B2
(45) Date of Patent: Nov. 25, 2025

(54) DRUG DISCHARGE ASSEMBLY AND DRUG INJECTION DEVICE COMPRISING SAME

(71) Applicant: IPV, Seoul (KR)

(72) Inventors: Jesse Jae Jin Kim, Seongnam-si (KR); Yong Joon Han, Seoul (KR)

(73) Assignee: IPV, Seoul (KR)

( * ) Notice: Subject to any disclaimer, the term of this patent is extended or adjusted under 35 U.S.C. 154(b) by 927 days.

(21) Appl. No.: 17/593,052

(22) PCT Filed: Dec. 23, 2019

(86) PCT No.: PCT/KR2019/018273
§ 371 (c)(1),
(2) Date: Sep. 7, 2021

(87) PCT Pub. No.: WO2020/184819
PCT Pub. Date: Sep. 17, 2020

(65) Prior Publication Data

US 2022/0176034 A1 Jun. 9, 2022

(30) Foreign Application Priority Data

Mar. 8, 2019 (KR) ........................ 10-2019-0027019
Oct. 4, 2019 (KR) ........................ 10-2019-0123367
Nov. 26, 2019 (KR) ........................ 10-2019-0153561

(51) Int. Cl.
*A61M 5/142* (2006.01)

(52) U.S. Cl.
CPC ............................... *A61M 5/14232* (2013.01)

(58) Field of Classification Search
CPC ........ A61M 5/14232; A61M 2205/103; A61M 2205/106; A61M 2205/3334;
(Continued)

(56) References Cited

U.S. PATENT DOCUMENTS

2005/0197625 A1* 9/2005 Haueter .............. A61M 5/1454 604/131
2008/0051711 A1* 2/2008 Mounce .............. A61M 5/1413 604/131

(Continued)

FOREIGN PATENT DOCUMENTS

EP 3017836 A1 5/2016
JP 2017512603 A 5/2017

(Continued)

OTHER PUBLICATIONS

International Search Report mailed Apr. 3, 2020 in International Application No. PCT/KR2019/018273 in 5 pages (including English translation of the ISR).

(Continued)

*Primary Examiner* — Dung T Ulsh
*Assistant Examiner* — Nelson Louis Alvarado, Jr.
(74) *Attorney, Agent, or Firm* — Knobbe, Martens, Olson & Bear, LLP

(57) ABSTRACT

The present disclosure provides a drug discharge assembly including a drive piece linearly reciprocated along one direction, a rotating unit being in contact with an end of the drive piece and rotating in one direction according to a linear reciprocating motion of the drive piece, a flexible tube disposed adjacent to the rotating unit and having a curved section at least partially extending in a circumferential direction, and a pressing unit mounted on the rotating unit and rotating while pressing the tube according to a rotation of the rotating unit, and a drug injection device comprising the same.

3 Claims, 14 Drawing Sheets

(58) Field of Classification Search
CPC ........... A61M 5/16809; A61M 5/14248; F04B 43/1253; F04B 43/1276
See application file for complete search history.

(56) References Cited

U.S. PATENT DOCUMENTS

| | | | |
|---|---|---|---|
| 2012/0165734 | A1 | 6/2012 | Auld et al. |
| 2014/0081202 | A1 | 3/2014 | Tsoukalis |

FOREIGN PATENT DOCUMENTS

| | | | |
|---|---|---|---|
| KR | 10-1999-0070632 | A | 9/1999 |
| KR | 10-0597601 | B1 | 7/2006 |
| KR | 10-2011-0027491 | A | 3/2011 |
| KR | 10-2012-0043258 | A | 5/2012 |
| WO | WO 2015/105916 | A1 | 7/2015 |

OTHER PUBLICATIONS

Written Opinion mailed Apr. 3, 2020 in International Application No. PCT/KR2019/018273 in 3 pages.
Notice of Allowance issued in Korean Patent Application No. 10-2019-0153561 dated Mar. 2, 2022 in 6 pages.
Office Action issued in Korean Patent Application No. 10-2021-0063472 dated Apr. 15, 2022 in 8 pages.
Notice of Allowance issued in Korean Patent Application No. 10-2021-0063472 dated Nov. 24, 2022 in 8 pages.

* cited by examiner

DRUG DISCHARGE ASSEMBLY AND DRUG INJECTION DEVICE COMPRISING SAME

CROSS-REFERENCE TO RELATED APPLICATIONS

This application is the U.S. National Phase under 35. U.S.C. § 371 of International Application PCT/KR2019/018273, filed Dec. 23, 2019, which claims priority to Korean Patent Application No. 10-2019-0027019, filed on Mar. 8, 2019, Korean Patent Application No. 10-2019-0123367, filed on Oct. 4, 2019, and Korean Patent Application No. 10-2019-0153561, filed on Nov. 26, 2019. The disclosure of each the above-described applications is hereby incorporated by reference in its entirety.

BACKGROUND

Field

The present disclosure relates to a drug discharge assembly and a drug injection device including the same.

Description of the Related Art

In general, drug injection devices such as insulin injection devices are used to inject a drug into a patient's body. The drug injection device is also used by professional medical staff such as a doctor or a nurse, but in most cases, it is used by the patient himself or a general person such as a guardian. In the case of diabetic patients, especially pediatric diabetic patients, a drug, such as insulin, needs to be injected into a human body at regular intervals. Therefore, drug injection devices in a form of patches that are attached to the human body for a certain period of time are being developed. These drug injection devices may be used in a state of being attached to a human body such as a patient's abdomen or waist for a certain period of time in the form of a patch.

The drug injection devices attached to the human body needs to be comfortable to wear, to be convenient to use, to be durable, and to be driven with low power. In particular, since the drug injection devices are attached to the patient's skin and used, a user should simply and conveniently insert a needle or cannula into the patient's skin.

Since it is important for the drug injection devices to inject drug quantitatively, there is a need for a device for distributing the drug quantitatively inside the device in order to inject drug quantitatively. Research on dispensing and discharging a drug in a constant amount by a mechanical method is continuing.

SUMMARY OF CERTAIN INVENTIVE ASPECTS

The present disclosure provides a drug discharge assembly and a drug injection device that a user may operate simply and accurately.

One aspect of the present disclosure provides a drug discharge assembly including a drive piece linearly reciprocated along one direction, a rotating unit being in contact with an end of the drive piece and rotating in one direction according to a linear reciprocating motion of the drive piece, a flexible tube disposed adjacent to the rotating unit and having a curved section at least partially extending in a circumferential direction, and a pressing unit mounted on the rotating unit and rotating while pressing the tube according to a rotation of the rotating unit.

The drug discharge assembly and drug injection device according to an embodiment of the present disclosure may quantitatively inject drug into a subject. When a drive shaft of a driving unit is linearly reciprocated, a rotation angle of a rotating unit is adjusted and an amount of drug moving along a curved section is controlled, so that the drug may be quantitatively discharged to a needle assembly.

A drug discharge assembly and a drug injection device according to an embodiment of the present disclosure may accurately discharge a small amount of drug by distributing the drug multiple times. Since a pressing portion of a pressing unit presses a tube, a preset amount of drug is firstly distributed between a pair of pressing points. Since the firstly distributed drug is distributed secondarily while moving a curved section, the drug discharge assembly accurately distributes a small amount of drug, and the drug injection device may quantitatively inject drug into a subject.

A drug discharge assembly and a drug injection device according to an embodiment of the present disclosure may accurately distribute drug with a simple driving mechanism. Even if an additional driving source is not provided in a reservoir, the drug may be moved from the reservoir to a needle assembly by rotating a pressing unit. The drug discharge assembly performs a function of distributing drug and acts as a driving source for moving drug, so that a structure of the drug injection device may be formed simply and compactly.

A drug discharge assembly and a drug injection device according to an embodiment of the present disclosure may quantitatively inject drug. Since a tube is branched from a rotating plate, a plurality of passages for moving and distributing the drug may be formed, so that a pressing portion may precisely and quantitatively distribute the drug.

A drug discharge assembly and a drug injection device according to an embodiment of the present disclosure may rapidly inject drug. Since a branched tube has different discharge cycles, the drug discharge assembly may quickly discharge drug.

A drug discharge assembly and a drug injection device according to an embodiment of the present disclosure may improve durability. Since the drug discharge assembly has a cover surrounding a tube, durability of the tube having a predetermined curvature may be improved. Of course, the scope of the present disclosure is not limited by these effects.

DETAILED DESCRIPTION OF CERTAIN ILLUSTRATIVE EMBODIMENTS

Figure 1:
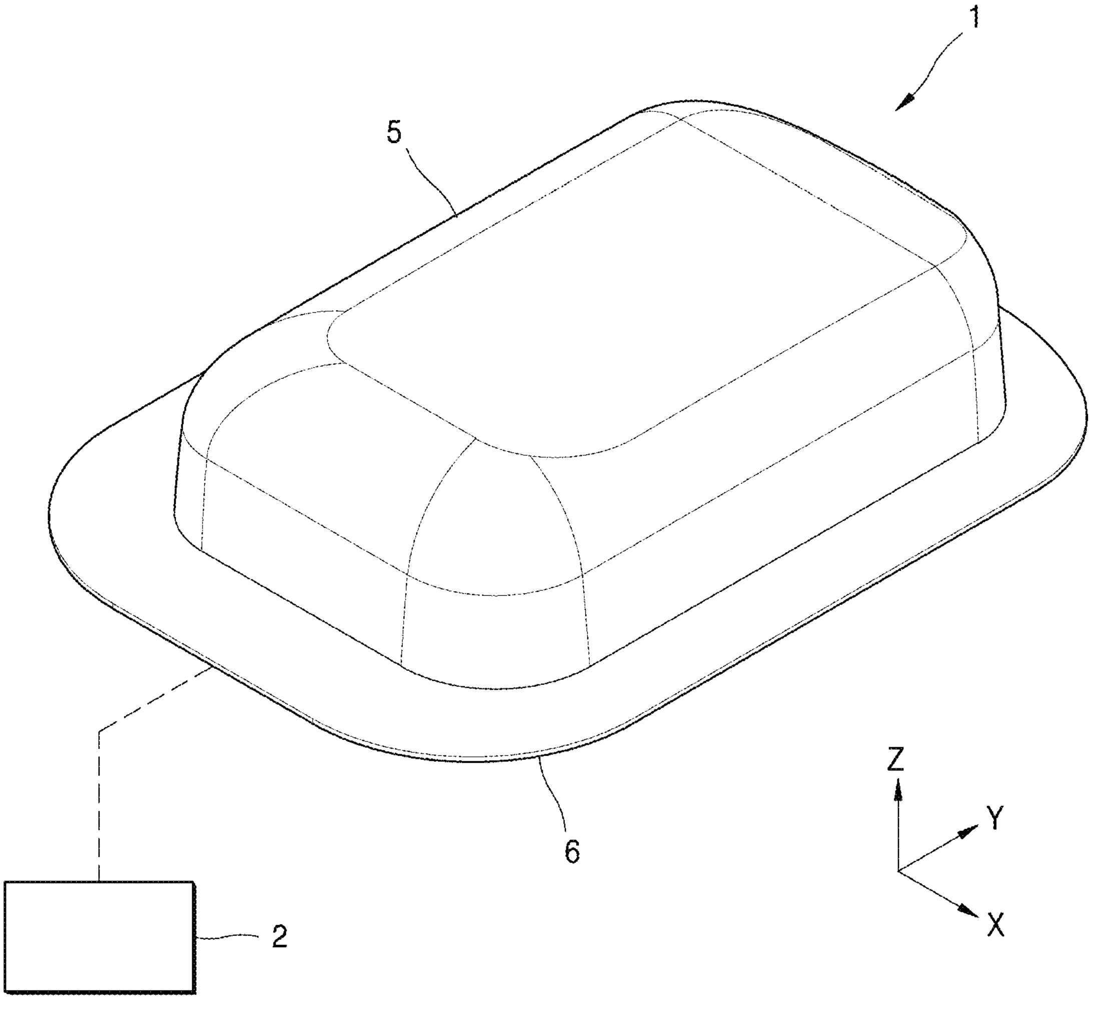
FIG. 1 is a perspective view illustrating a drug injection device according to an embodiment of the present disclosure.

One aspect of the present disclosure provides a drug discharge assembly including a drive piece linearly reciprocated along one direction, a rotating unit being in contact with an end of the drive piece and rotating in one direction according to a linear reciprocating motion of the drive piece, a flexible tube disposed adjacent to the rotating unit and having a curved section at least partially extending in a circumferential direction, and a pressing unit mounted on the rotating unit and rotating while pressing the tube according to a rotation of the rotating unit.

In addition, the drive piece may include a body, a first arm extending from the body and having a first bent end bent at a preset angle with respect to a length direction at an end thereof, and a second arm disposed in parallel with the first arm and having a second bent end bent in a direction different from the first bent end at an end thereof.

In addition, the first bent end and the second bent end may alternately press the rotating unit when the drive piece is in a linear reciprocating motion.

In addition, the pressing unit may press the tube when the pressing unit contacts the curved section of the tube so that the tube is compressed at a contact point.

Another aspect of the present disclosure provides a drug injection device including a needle assembly, a reservoir storing a drug discharged to the needle assembly, a drive module linearly reciprocating a drive shaft, a drive piece connected to the drive shaft and linearly reciprocated according to a movement of the drive shaft, a rotating unit being in contact with an end of the drive piece and rotating in one direction according to a linear reciprocating motion of the drive piece, a flexible tube disposed between the needle assembly and the reservoir and having a curved section at least partially extending in a circumferential direction, and a pressing unit mounted on the rotating unit and rotating while pressing the tube according to a rotation of the rotating unit.

Another aspect of the present disclosure provides a drug discharge assembly including a rotating plate rotating in one direction, a flexible tube partially extending in a circumferential direction of the rotating plate, a pressing portion mounted on a surface of the rotating plate to press the tube when the rotating plate is rotated, and a guide portion extending along the circumferential direction of the rotating plate and supporting the tube.

In addition, the tube may be disposed to be spaced apart from the surface of the rotating plate, and may have a curved portion that is branched from an inlet end to an outlet end and extends in the circumferential direction in parallel.

In addition, the pressing portion may include a first roller for pressing one of the branched curved portions and a second roller for pressing the other, and the first roller and the second roller may be disposed to deviate from each other.

In addition, the curved portion may extend to both surfaces of the rotating plate, the first roller may be disposed on one surface of the rotating plate, and the second roller may be disposed on the other surface of the rotating plate.

In addition, the pressing portion may have a plurality of rollers spaced apart at preset intervals along the circumferential direction of the rotating plate. In addition, it may further include a cover provided to surround the tube pressed by the pressing portion.

Another aspect of the present disclosure provides a drug injection device including a needle, a reservoir for storing drug discharged by the needle, a drug discharge assembly disposed between the needle and the reservoir and distributing the drug to the needle quantitatively, and a driving unit for driving the drug discharge assembly, wherein the drug discharge assembly includes a rotating plate connected to the driving unit and rotates in one direction, a flexible tube partially extending in a circumferential direction of the rotating plate, a pressing portion is mounted on a surface of the rotating plate and press the tube when the rotating plate is rotated, and a guide portion extending along the circumferential direction of the rotating plate and supporting the tube.

In addition, the tube may be disposed to be spaced apart from the surface of the rotating plate, and may have a curved portion that is branched from an inlet end to an outlet end and extends in the circumferential direction in parallel.

In addition, the pressing portion may include a first roller for pressing one of the branched curved portions and a second roller for pressing the other, and the first roller and the second roller may be disposed to deviate from each other.

In addition, the driving unit may include a driving gear engaged with the rotating plate, and a drive piece inserted into teeth of the driving gear and rotating the driving gear in one direction during linear reciprocation.

In the present disclosure, various transformations may be applied and various embodiments may be provided, and specific embodiments will be illustrated in the drawings and described in detail in the detailed description. Effects and features of the present disclosure, and a method of achieving them will be apparent with reference to embodiments described later in detail together with the drawings. However, the present disclosure is not limited to the embodiments disclosed below and may be implemented in various forms.

Hereinafter, embodiments of the present disclosure will be described in detail with reference to the accompanying drawings, and when describing with reference to the drawings, the same or corresponding constituent elements are assigned the same reference numerals, and redundant descriptions thereof will be omitted.

In the following examples, expressions in the singular include plural expressions unless the context clearly indicates otherwise.

In the following embodiments, terms such as include or have means that the features or elements described in the specification are present, and do not preclude the possibility that one or more other features or components may be added.

When a certain embodiment can be implemented differently, a specific process order may be performed differently from the described order. For example, two processes described in succession may be performed substantially simultaneously, or may be performed in an order opposite to the described order.

In the drawings, components may be exaggerated or reduced in size for convenience of description. For example, the size and thickness of each component shown in the drawings are arbitrarily shown for convenience of description, and thus the following embodiments are not necessarily limited to those shown.

FIG. 1 is a perspective view illustrating a drug injection device 1 according to an embodiment of the present disclosure.

Referring to FIG. 1, a drug injection device 1 is attached to a drug injection subject, and may inject drug stored therein to a user in a set amount. In an optional embodiment, the drug injection device 1 may be mounted on the user's body. In addition, as another optional embodiment, the drug injection device 1 may be mounted on an animal to inject drug.

The drug injection device 1 may be used for various purposes depending on the type of drug to be injected. For example, the drug may include insulin-based drug for diabetics, and may include drug for pancreas, drug for heart, and other various types of drug.

The drug injection device 1 may be connected to a remote device 2 connected by wire or wirelessly. The user may use the drug injection device 1 by manipulating the remote device 2, and may monitor the state of use of the drug injection device 1. For example, the amount of drug injected from the drug injection device 1, the number of injections of the drug, the amount of drug stored in a reservoir, the user's bio information, etc. may be monitored, based on this, the user may drive the drug injection device 1.

In one embodiment, the remote device 2 refers to a communication terminal capable of using an application in a wired or wireless communication environment. Here, the remote device 2 may be the user's portable terminal. In more detail, the remote device 2 may include a computer (e.g. desktop, laptop, tablet, etc.), a media computing platform (e.g. cable, satellite set-top box, digital video recorder), a handheld computing device (e.g. PDA, e-mail client, etc.), a mobile phone in any form, a form of a wearable device that can be attached or mounted on the user's body, or any form of another kind of computing or communication platform, but the present disclosure is not limited thereto.

The drug injection device 1 and the remote device 2 may communicate through a communication network. In this case, the communication network refers to a communication network providing an access path so that the remote device 2 may transmit and receive data after accessing the service server (not illustrated). The communication network may be, for example, wired networks such as local area networks (LANs), wide area networks (WANs), metropolitan area networks (MANs), integrated service digital networks (ISDNs), etc. or wireless networks such as wireless LANs, CDMA, Bluetooth, satellite communications, etc., but the scope of the present disclosure is not limited thereto.

According to FIG. 1, the remote device 2 is illustrated to be a single device, but the present disclosure is not necessarily limited thereto, and may include a plurality of devices capable of communicating with the drug injection device 1.

Figure 3:
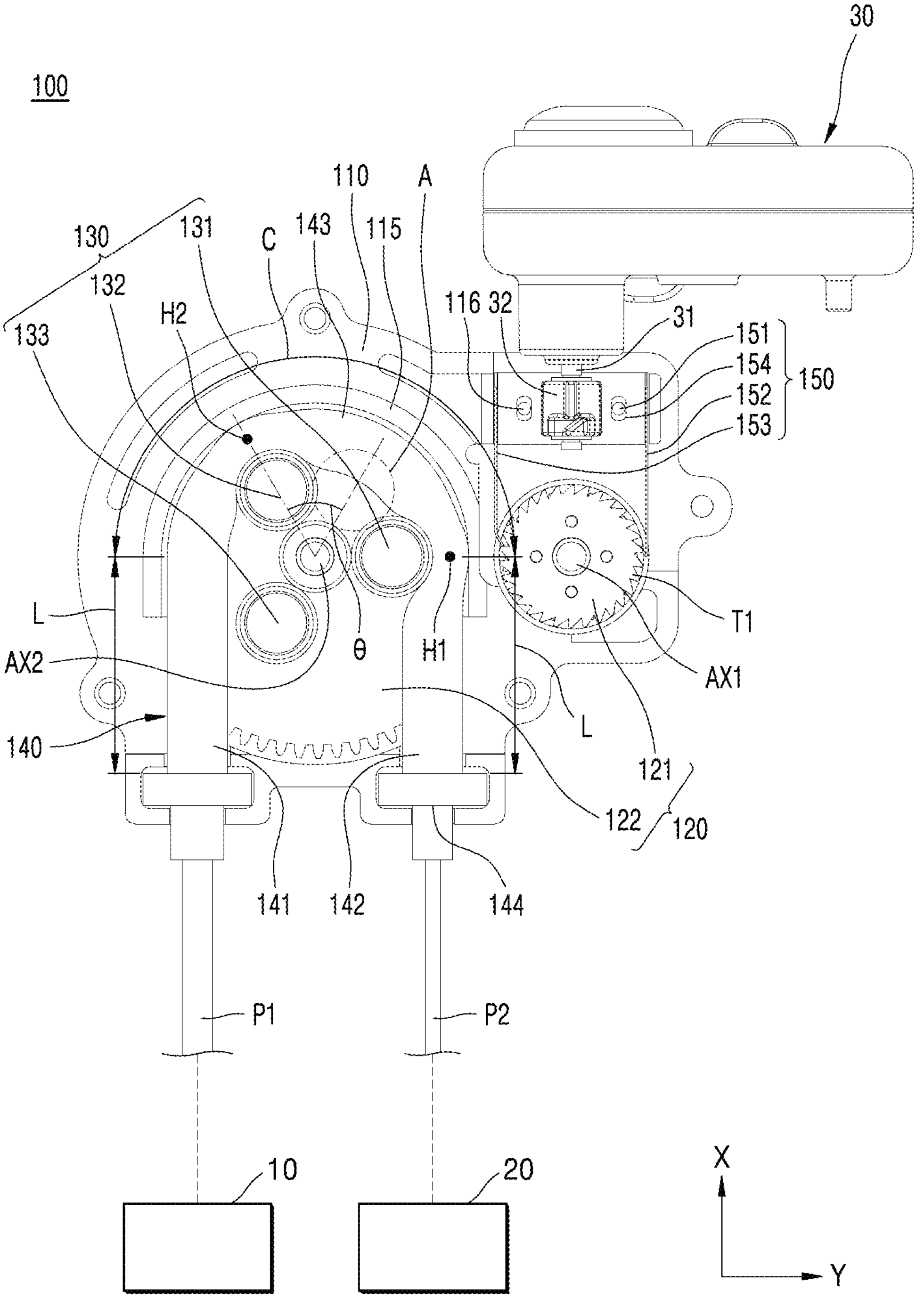
FIG. 3 is a plan view illustrating the drug discharge assembly of FIG. 2.
Figure 7:
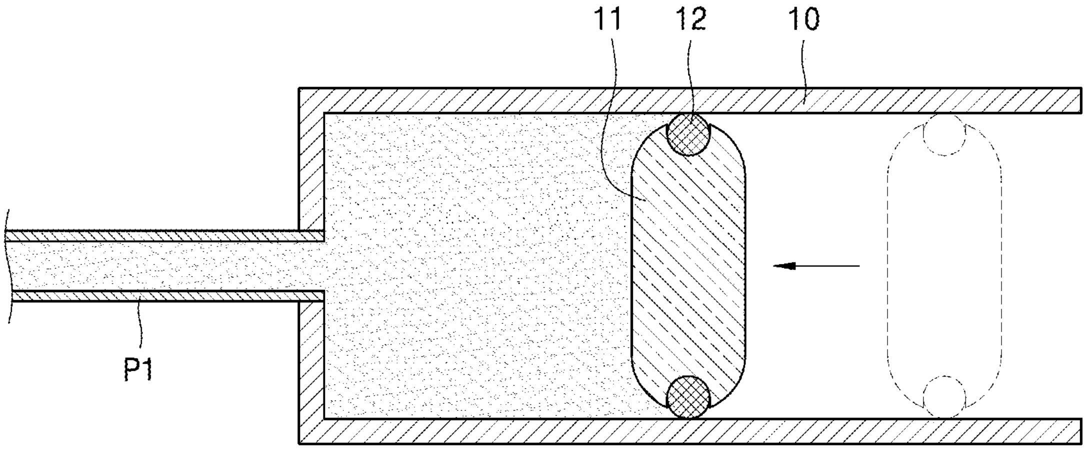
FIG. 7 is a diagram illustrating a reservoir connected to the drug discharge assembly of FIG. 2.

The drug injection device 1 may include a housing 5 covering an outside and an attachment 6 attached to the user's skin, and a plurality of parts are disposed in an inner space of the housing 5. Referring to FIGS. 3 and 7, the drug injection device 1 may include a reservoir 10, a needle assembly 20, a drive module 30, and a drug discharge assembly 100.

The reservoir 10 stores drug to be injected and is connected to the drug discharge assembly 100. The reservoir 10 may be mounted inside the housing 5. In another embodiment, the reservoir 10 may be provided outside the housing 5 as well.

The needle assembly 20 is disposed on one side of the housing 5. Since the needle assembly 20 is inserted into the user's skin, the drug to be discharged may be injected into the user. The drug discharge assembly 100 is provided between the needle assembly 20 and the reservoir 10, so that the drug may be distributed at a preset quantity or at a preset period and discharged to the needle assembly 20.

The drive module 30 is disposed in the inner space of the housing 5, and may transmit a driving force to the drug discharge assembly 100. In one embodiment, the drive module 30 and the drug discharge assembly 100 may be disposed in separate configurations, respectively. In another embodiment, the drive module 30 may be configured as a component constituting the drug discharge assembly 100.

Figure 2:
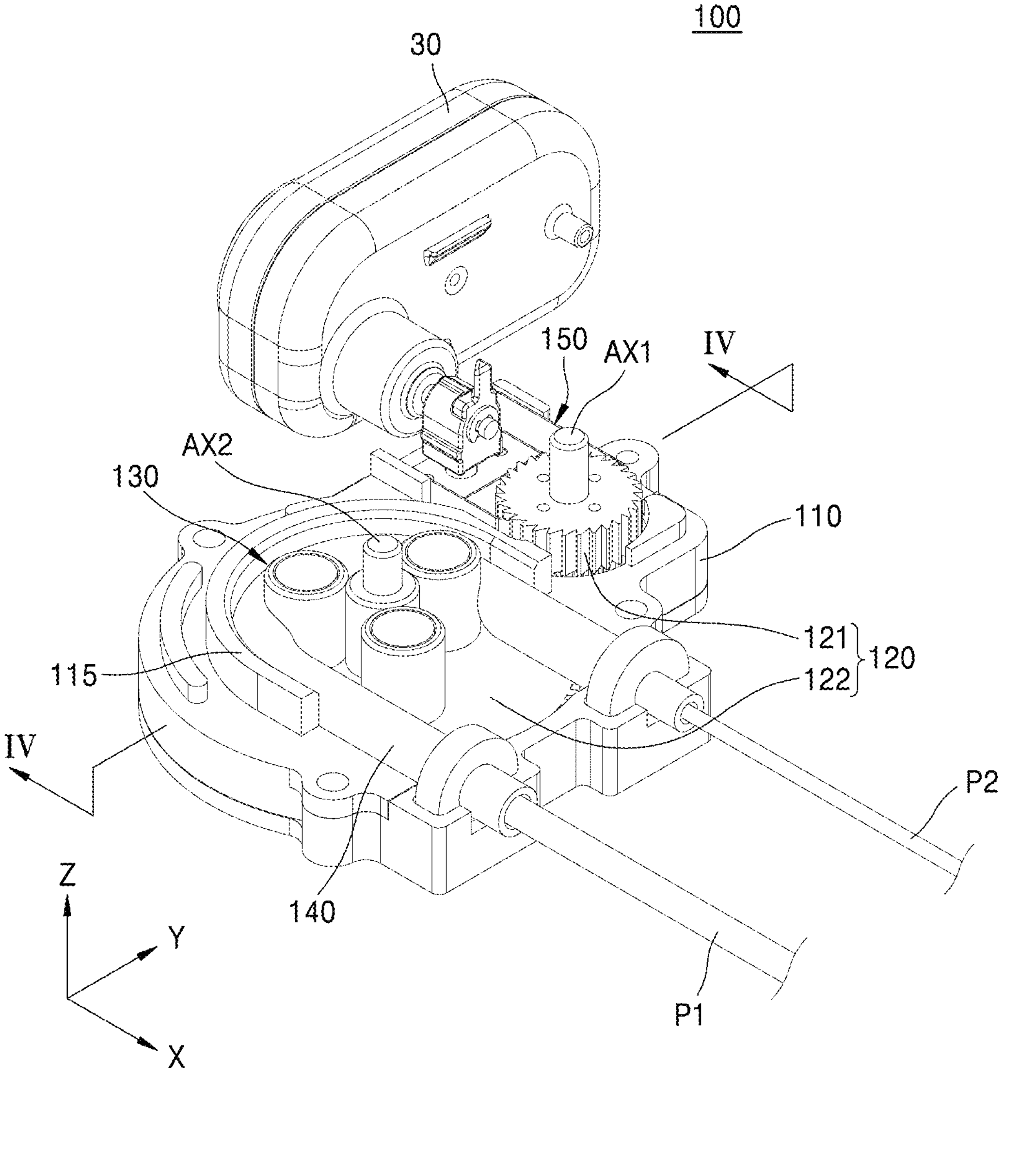
FIG. 2 is a perspective view illustrating a drug discharge assembly according to an embodiment of the present disclosure.

Referring to FIG. 2, the drive module 30 may include a drive shaft 31 linearly reciprocating in one direction. When the drive module 30 is driven, the drive shaft 31 may repeatedly advance and retreat along one direction, that is, a longitudinal direction. A joint 32 may be provided on one side of the drive shaft 31. The joint 32 is connected to a drive piece 150, and the drive piece 150 may be linearly reciprocated by the linear reciprocating motion of the drive shaft 31.

All kinds of devices having drug suction power and drug discharge power by electricity may be used as the drive module 30. For example, all types of pumps such as a mechanical displacement micro-pump and an electromagnetic motion micro-pump may be used. The mechanical displacement micro-pump is a pump that uses the motion of a solid or fluid such as a gear or diagram to generate a pressure difference to induce a flow of fluid, and includes a diaphragm displacement pump, a fluid displacement pump, rotary pump, etc. The electromagnetic motion micro-pump is a pump that directly uses energy in an electrical or magnetic form to move a fluid, and includes an electro hydrodynamic pump (EHD), an electro osmotic pump, and a magneto hydrodynamic pump, an electro wetting pump, etc.

Figure 4:
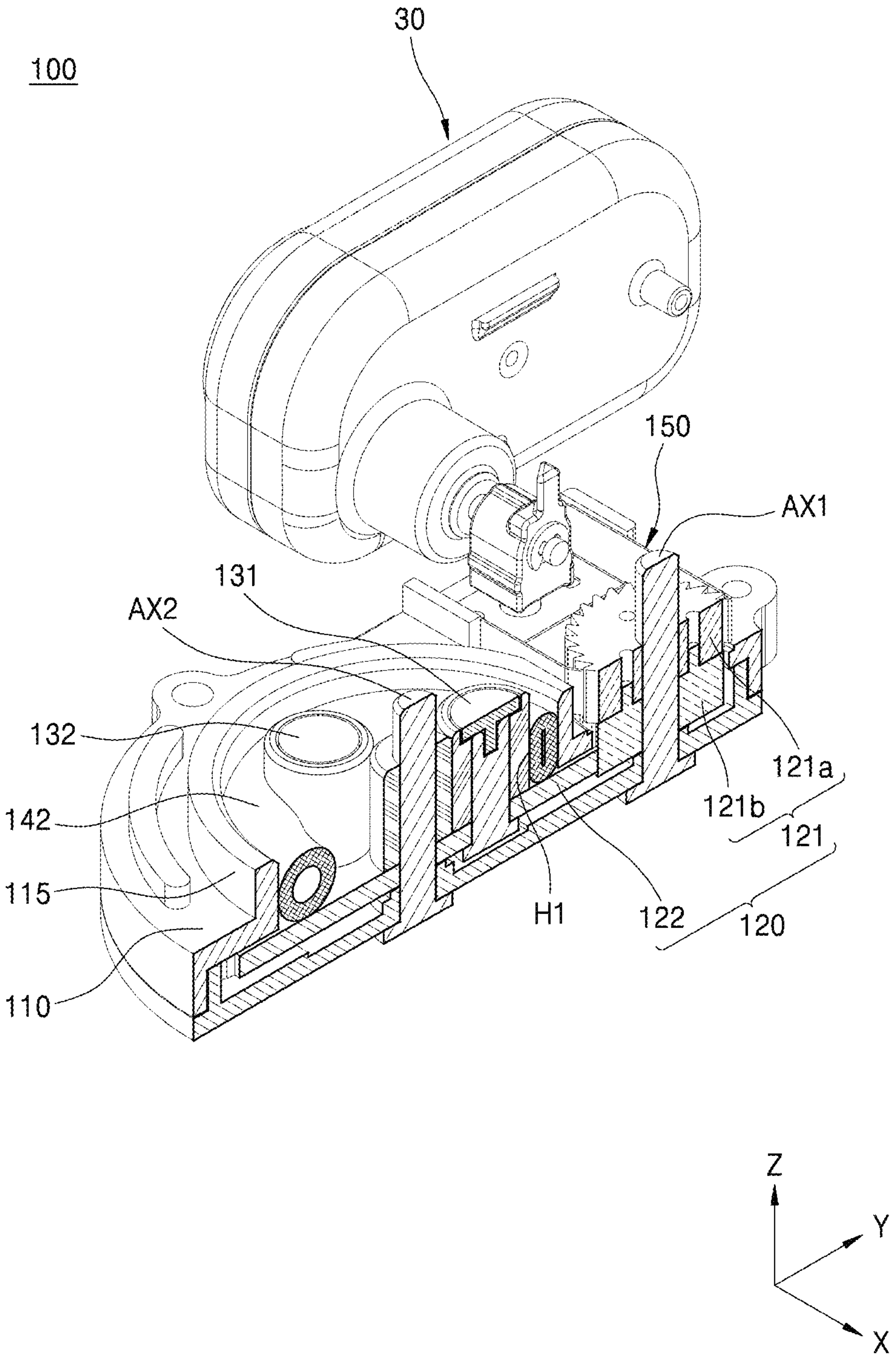
FIG. 4 is a cross-sectional view taken along IV-IV of FIG. 2.

FIG. 2 is a perspective view illustrating a drug discharge assembly 100 according to an embodiment of the present disclosure, FIG. 3 is a plan view illustrating the drug discharge assembly 100 of FIG. 2, and FIG. 4 is a cross-sectional view taken along IV-IV of FIG. 2.

Referring to FIGS. 2 to 4, the drug discharge assembly 100 includes a base 110, a rotating unit 120, a pressing unit 130, a tube 140, and the drive piece 150, and the drive module 30 may be connected to the drive piece 150.

The base 110 may form an appearance of the drug discharge assembly 100. At least one of the rotating unit 120, the pressing unit 130, the tube 140, and the drive piece 150 may be provided and supported on the base 110. The base 110 is mounted on the housing 5, and the drug discharge assembly 100 may be provided in the inner space of the drug injection device 1.

The base 110 may include a guide portion 115. The guide portion 115 extends along a circumferential direction of a second rotating member 122 and may support the tube 140. A part of the guide portion 115 protrudes from one surface of the base 110, and may extend along a curved section C of the tube 140. In addition, another part of the guide portion 115 may also extend in a straight section L of the tube 140.

The guide portion 115 may support a force applied by the pressing unit 130 to guide the movement of the drug. When the pressing unit 130 presses the tube 140, the guide portion

115 supports the tube 140 on the opposite side of the pressing unit 130. When the pressing unit 130 presses the tube 140 in the curved section C, at the pressing points H1 and H2 where the tube 140 and the pressing portion contact each other, the tube 140 may be compressed so that an inner cross-sectional area through which the drug flows becomes zero. At this time, when the pressing unit 130 is rotated, the drug of the tube 140 is also moved. In one embodiment, the guide portion 115 may be disposed outside the curved section C, and a region in which the pressing unit 130 applies the tube 140 may be disposed inside the curved section C.

The drawing illustrates an embodiment in which the guide portion 115 is disposed outside the tube 140, and the pressing unit 130 is disposed inside the tube 140, but is not limited thereto, in another embodiment, the guide portion may be disposed inside the tube, and the pressing unit may be disposed outside the tube.

The guide portion 115 protrudes from the base 110 so as to align the position of the tube 140. Since the guide portion 115 is formed along the curved section C, and the tube 140 extends along the guide portion 115, the guide portion 115 may form and align the curved section C.

The base 110 may have a guide protrusion 116. The guide protrusion 116 protrudes from one surface of the base 110 and may be inserted into the guide hole 154 of the drive piece 150. In one embodiment, the guide protrusion 116 may be provided in a pair and inserted into a pair of guide holes 154, respectively, to guide movement of the drive piece 150.

Figure 5:
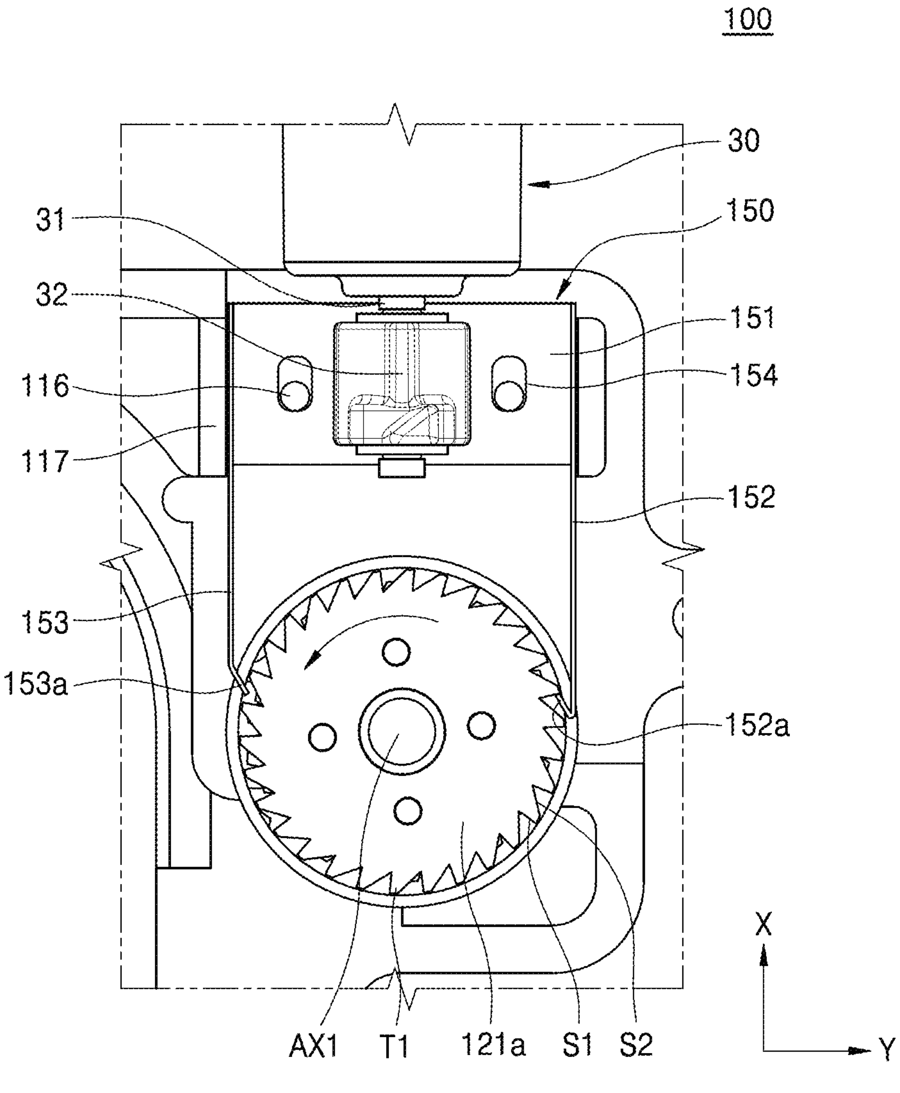
FIGS. 5 and 6 are each a diagram illustrating a driving of a drug discharge assembly.

Referring to FIG. 5, the base 110 may have a guide wall 117. The guide wall 117 protrudes from one surface of the base 110 and may guide the movement of the drive piece 150. The guide wall 117 is disposed adjacent to the guide protrusion 116, and may support a first arm 152 and a second arm 153 of the drive piece 150.

By the guide protrusion 116 and the guide wall 117, linear reciprocating motion of the drive piece 150 may be guided. The guide protrusion 116 is inserted into the guide hole 154, and the first arm 152 and the second arm 153 are respectively inserted into the guide wall 117 extending in the moving direction, so that the drive piece 150 may be moved along a preset trajectory during linear motion.

The rotating unit 120 is mounted on one side of the base 110, and may be rotated by receiving a driving force from the drive module 30. The rotating unit 120 is in contact with an end of the drive piece 150, and may be rotated in one direction according to the linear reciprocating motion of the drive piece 150. The rotating unit 120 may be defined as a configuration capable of rotating a pressing portion 130 by rotating at least a portion thereof by receiving a driving force from the drive module 30.

In an embodiment, a plurality of members may be drivingly connected to each other in the rotating unit 120. The rotating unit 120 may include a first rotating member 121 and a second rotating member 122.

The first rotating member 121 is in contact with the end of the drive piece 150 and rotated according to a linear reciprocating motion of the drive piece 150. The second rotating member 122 may be connected to the first rotating member 121 and rotated according to the rotation of the first rotating member 121.

The first rotating member 121 may include a first rotating gear 121*a* disposed to contact at least one of the first arm 152 and the second arm 153 of the drive piece 150. The first rotating gear 121*a* may be rotated about a first axis AX1 by receiving a driving force from the drive piece 150.

The first rotating gear 121*a* may include a plurality of first teeth T1. Referring to FIG. 5, the first teeth T1 are disposed in a circumferential direction of the first rotating gear 121*a* and may have a first surface S1 and a second surface S2, wherein the length of the first surface S1 is different from the length of the second surface S2. This will be described in detail below.

The first rotating member 121 may include a second rotating gear 121*b* disposed opposite to the first rotating gear 121*a*. The first rotating gear 121*a* and the second rotating gear 121*b* are integrally formed, and receiving a driving force from the first rotating gear 121*a*, the second rotating gear 121*b* may also rotate around the first axis AX1.

The second rotating member 122 has a plate shape and may be rotated about a second axis AX2. The second rotating member 122 is connected to the second rotating gear 121*b*. A second teeth of the second rotating gear 121*b* and a third teeth of the second rotating member 122 are connected to each other, and the second rotating member 122 may be rotated by the rotation of the second rotating gear 121*b*.

A rotation angle of the second rotating member 122 may be determined by the number of movements of the drive shaft 31, the number of first teeth, the number of second teeth, and the number of third teeth. In detail, a rotation angle of the first rotating member 121 according to the drive of the drive shaft 31 is set by the number of first teeth. In addition, the rotation angle of the second rotating member 122 according to the drive of the drive shaft 31 may be determined by a ratio of the number of first teeth and the number of second teeth, and a ratio of the number of second teeth and the number of third teeth. Accordingly, the amount of drug discharged according to one drive of the drive module 30 may be adjusted by adjusting the number of first teeth, the number of second teeth, and the number of third teeth.

In another embodiment, the rotating unit may be provided as one rotating member, and may receive a driving force directly from the drive module. The drive piece may directly rotate the rotating member by pressing the rotating member on which the pressing portion is provided. When the drive shaft of the drive module is linearly moved, the drive piece is linearly moved together so that the rotating member may be rotated. The pressing portion provided on the rotating member may press the tube to discharge drug.

The pressing unit 130 is mounted on the rotating unit 120 and may be rotated together with the rotating unit 120. The pressing unit 130 may press the tube 140 while being rotated around the second axis AX2. When the pressing unit 130 contacts the curved section C of the tube 140, the tube 140 may be pressed so that the tube 140 is compressed at the contact point.

The pressing unit 130 may include a plurality of rollers. When the drug discharge assembly 100 is driven, at least one pressing portion may be disposed in the curved section C. More preferably, when the pressing unit 130 rotates, at least two or more pressing portions may form the pressing points H1 and H2 in the curved section C.

As described above, at a point where the pressing portion of the pressing unit 130 and the tube 140 contact each other, the tube is pressed by the pressing portion, so that the inner cross-sectional area of the tube 140 is formed to be zero. Since at least two or more of the pressing points H1 and H2 are formed in the curved section C, a quantitative drug may be discharged according to the rotation angle of the second rotating member 122. In detail, since the amount of drug does not change between the two pressing points H1 and H2 formed by the pressing portion in the curved section C, it is firstly and quantitatively distributed. Thereafter, the firstly distributed drug may be secondary and quantitatively discharged by the rotation of the second rotating member 122.

In the pressing unit 130, the number of pressing portions may be set according to the length of the curved section C. The pressing portion may be determined by a central angle of the curved section. The number of pressing portions may be set according to the following equation.

$$N>360°/\text{central angle (degree) of curved section} \qquad \text{[Equation]}$$

N is the number of the pressing portions provided in the pressing unit 130, and the central angle of the curved section is defined as a central angle of the curved section C around the second axis AX2.

In one embodiment, as shown in FIG. 3, if the central angle of the curved section C is 180 degrees, the number of the pressing portions forming the pressing unit 130 may be set to three or more. When the central angle of the curved section C is formed at 180 degrees and three or more pressing portions are provided, at least two pressing points H1 and H2 may always be formed in the curved section C. Therefore, in order to distribute the drug firstly by the pressing points H1 and H2 in the curved section C, the number of pressing portions may be set according to the equation.

In one embodiment, the pressing unit 130 may include a first pressing portion 131, a second pressing portion 132, and a third pressing portion 133. The first pressing portion 131, the second pressing portion 132, and the third pressing portion 133 disposed at equal intervals form the pressing points together with the tube 140, and when the second rotating member 122 is rotated, the pressing points H1 and H2 are moved along the curved section C.

In one embodiment, the pressing unit 130 may include a contact cover 134 having a predetermined hardness outside each of the pressing portions. The contact cover 134 may include a material having a predetermined cushion, may gently press the flexible tube 140, and may completely compress the tube 140.

The tube 140 is disposed adjacent to the rotating unit 120, and at least a portion may have the curved section extending in the circumferential direction. The tube 140 may include a flexible material and may be compressed by the pressing portion of the pressing unit 130.

The tube 140 may be provided between the reservoir 10 and the needle assembly 20 and may be provided to pass through the rotating unit 120. Part of the tube 140 may extend in the circumferential direction of the second rotating member 122.

The tube 140 may include an inlet end 141 connected to the reservoir 10 through a first conduit P1 and an outlet end 142 connected to the needle assembly 20 through a second conduit P2. In addition, a curved portion 143 is formed between the inlet end 141 and the outlet end 142, and the curved portion 143 may extend along the circumferential direction of the second rotating member 122. The inlet end 141 and the outlet end 142 may form the straight section L, and the curved portion 143 may form the curved section C.

In one embodiment, referring to FIG. 3, the curved portion 143 may have a central angle of 180 degrees around the second axis AX2. However, the central angle of the curved portion 143 is not limited thereto, and may be variously set according to the discharge amount of the drug and the number of the pressing portions.

In the curved section C, the tube 140 is compressed by the pressing portion, so that the inner cross-sectional area of the tube 140 at the pressing points H1 and H2 may be formed to zero. On the other hand, in the straight section L, while contacting or pressing force between the pressing portion and the tube 140 is released, the drug may be discharged to the outlet end 142 according to the movement of the pressing portion.

The tube 140 may include a fixing block 144 mounted on the base 110. The fixing block 144 is disposed at the inlet end 141 and the outlet end 142, respectively, and the fixing block 144 is mounted on the base 110 so that the position of the tube 140 may be fixed.

The drive piece 150 may be disposed between the drive module 30 and the rotating unit 120 to transmit a driving force generated by the drive module 30 to the rotating unit 120. The drive piece 150 is connected to the drive shaft 31, and may be linearly reciprocated according to the movement of the drive shaft 31.

The drive piece 150 may include a body 151, the first arm 152, the second arm 153, and the guide hole 154.

The body 151 may be connected to the drive shaft 31. In detail, the joint 32 is disposed between the body 151 and the drive shaft 31, so that when the drive shaft 31 is linearly reciprocated, the body 151 may also be linearly reciprocated.

The first arm 152 may extend from one side of the body 151. A first bent end 152*a* bent at a preset angle with respect to the length direction may be formed at an end of the first arm 152. Referring to FIG. 5, the first bent end 152*a* is bent toward the drive module 30, but may have a bending angle smaller than 90 degrees in the longitudinal direction of the first arm 152.

The second arm 153 may extend from the other side of the body 151 and may be disposed parallel to the first arm 152. An end of the second arm 153 may have a second bent end 153*a* bent in a direction different from that of the first bent end 152*a*. Referring to FIG. 5, the second bent end 153*a* extends in a direction away from the drive module 30, and may have a bending angle that exceeds 90 degrees in the length direction of the second arm 153.

Since the first arm 152 and the second arm 153 may have a predetermined elasticity, when the drive piece 150 is linearly reciprocated in the front-rear direction, the first bent end 152*a* and the second bent end 153*a* may press the first surface S1 of the first teeth T1 or may move along the second surface S2 of the first teeth T1.

The guide hole 154 may be provided in the body 151, and may have an opening area larger than the cross section of the guide protrusion 116. Since the guide hole 154 has a long hole shape, when the drive piece 150 is linearly reciprocated, it may be moved along the guide protrusion 116.

Figure 6:
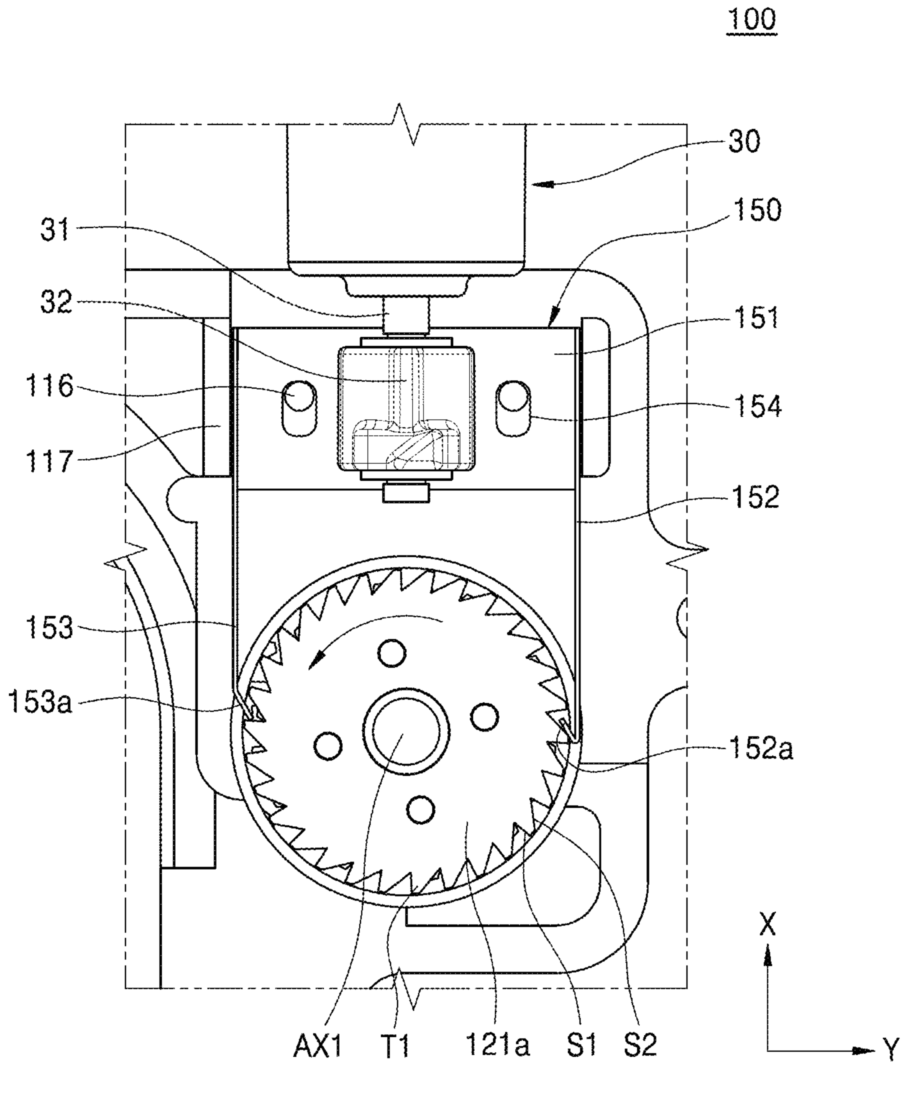

FIGS. 5 and 6 is a diagram illustrating a driving of a drug discharge assembly 100.

Referring to FIGS. 5 and 6, in the drug discharge assembly 100 may quantitatively discharge drug by linearly reciprocating the drive shaft 31 in the front-rear direction.

Hereinafter, forward movement is defined as the drive shaft 31 moving toward the first axis AX1, and backward movement is defined as the drive shaft 31 moving toward the drive module 30.

The first teeth T1 may have the first surface S1 and the second surface S2 having different lengths in an oblique direction. The length of the first surface S1 is formed smaller than the length of the second surface S2. That is, the second surface S2 may have a smoother slope than the first surface S1.

When the first bent end 152*a* or the second bent end 153*a* press the first surface S1, the first rotating member 121 may rotate in one direction. On the other hand, in the case of the second surface S2, the first bent end 152*a* or the second bent end 153*a* may move beyond the second surface S2. Since the drive piece 150 transmits a driving force only to the first surface S1, the first rotating member 121 may rotate in only one direction.

As illustrated in FIG. 5, when the drive shaft 31 moves backward, the first bent end 152*a* moves backward in contact with the first surface S1, so that the first rotating member 121 may rotate by one tooth angle. At this time, the second bent end 153*a* is moved along the second surface S2.

As illustrated in FIG. 6, when the drive shaft 31 moves forward, the second bent end 153*a* moves forward in contact with the first surface S1, so that the first rotating member 121 may be rotated by the one tooth angle. At this time, the first bent end 152*a* is moved along the second surface S2.

Since the first bent end 152*a* and the second bent end 153*a* are bent in different directions, and the first surface S1 and the second surface S2 of the first teeth T1 have different inclinations, the first rotating member 121 may be moved in only one direction by the linear reciprocating motion of the drive piece 150.

The rotating unit 120 is always drivingly connected to any one of the first bent end 152*a* and the second bent end 153*a*. When the drive piece 150 is linearly reciprocated, the first bent end 152*a* and the second bent end 153*a* alternately press the rotating unit 120. When the drive piece 150 is linearly reciprocated in the front-rear direction, the first bent end 152*a* or the second bent end 153*a* always presses the first surface S1 of the first teeth T1, so the first rotating member 121 may be continuously rotated.

When the first rotating member 121 is rotated, the second rotating member 122 may also be rotated. According to the rotation of the second rotating member 122, the pressing unit 130 may press the tube 140 to firstly distribute the drug. Since the cross-sectional area of the tube 140 becomes zero at the point where the pressing portion of the pressing unit 130 and the tube 140 contact and press, the drug is firstly distributed in the space between the pair of pressing points H1 and H2.

When the second rotating member 122 is rotated, the pressing unit 130 is also moved together to move the firstly distributed drug to the needle assembly 20 to finally quantitatively discharge. According to the driving mechanism as described above, the drug is distributed twice while passing through the drug discharge assembly 100, so that a quantitative drug may be discharged to the needle assembly 20.

The pressing unit 130 may adjust the amount of drug to be firstly distributed by adjusting the number of the pressing portions. For example, when the number of pressing portions is increased, the amount of drug to be firstly distributed may be set to be small, and the drug to be finally discharged may be accurately quantitatively injected.

The drug discharge assembly 100 may control the amount of drug to be discharged by the rotation angle of the rotating unit 120 and the length in the radial direction of the rotating unit 120. The rotation angle of the rotating unit 120 and the length in the radial direction of the rotating unit 120 set the moving distance of the drug in the curved section C. Since the rotation angle of the second rotating member 122 and the radial distance of the second rotating member 122 based on the second axis AX2 set the moving distance of the drug, the drug may be quantitatively discharged.

Referring to FIG. 3, when the second rotating member 122 is rotated by θ, the second pressing portion 132 is also rotated and moved to a position A. When the rotation angle of the second rotating member 122 is adjusted, the pressing point of the second pressing portion 132 is moved, so that the amount of drug to be discharged may be accurately controlled.

FIG. 7 is a diagram illustrating a reservoir 10 connected to the drug discharge assembly 100 of FIG. 2.

Referring to FIGS. 3 and 7, since the drug is moved from the reservoir 10 to the needle assembly 20 by driving the drug discharge assembly 100, an additional driving source for discharging the drug to the reservoir 10 is unnecessary.

The reservoir 10 has a space for storing drug therein. One side of the reservoir 10 is connected to the tube 140 by the first conduit P1, and a plunger 11 is disposed on the other side. In the plunger 11, a sealing member 12 is disposed at a portion in contact with an inner wall of the reservoir 10, so that leakage of drug through the plunger 11 may be prevented.

Conventionally, in order to discharge drug from a reservoir to a needle assembly, a drive module accurately pushes the plunger, and the drug is discharged to the needle assembly by the movement of the plunger. However, there is a limitation in implementing a mechanism that precisely moves the plunger to discharge drug quantitatively.

The drug discharge assembly 100 may quantitatively discharge the drug stored in the reservoir 10 to the needle assembly 20 without providing the additional driving source to the reservoir 10.

As the pressing portions of the drive module 30 rotate while pressing the tube 140, the drug existing in the tube 140 moves to the needle assembly 20. When the drug existing in the tube 140 is discharged to the needle assembly 20, the drug stored in the reservoir 10 is introduced into an empty space of the tube 140 again. Therefore, even if the additional driving source is not provided to the reservoir 10, the drug of the reservoir 10 is moved to the tube 140 along the first conduit P1, and the drug quantitatively distributed from the drug discharge assembly 100 is moved to the second conduit P2 and discharged to the needle assembly 20.

The drug discharge assembly 100 and the drug injection device 1 according to an embodiment of the present disclosure may quantitatively inject drug into the subject. When the drive shaft 31 of the drive module 30 is linearly reciprocated, the rotation angle of the rotating unit 120 is adjusted, and the amount of drug moving along the curved section C is controlled, so that the drug may be quantitatively discharged to the needle assembly 20.

The drug discharge assembly 100 and the drug injection device 1 according to an embodiment of the present disclosure may distribute the drug multiple times to accurately discharge a small amount of drug. Since the pressing portion of the pressing unit 130 presses the tube 140, a preset amount of drug is firstly distributed between the pair of pressing points H1 and H2. Since the firstly distributed drug is secondarily distributed while moving the curved section C, the drug discharge assembly 100 accurately distributes a small amount drug, and the drug injection device 1 may quantitatively inject the drug to the subject.

The drug discharge assembly 100 and the drug injection device 1 according to an embodiment of the present disclosure may accurately distribute drug with a simple driving mechanism. Even if the additional driving source is not provided to the reservoir 10, the drug may be moved from the reservoir 10 to the needle assembly 20 due to the rotation of the pressing unit 130. Since the drug discharge assembly 100 performs a function of distributing drug and acts as a driving source for moving drug, the structure of the drug injection device 1 may be formed simply and compactly.

Figure 8:
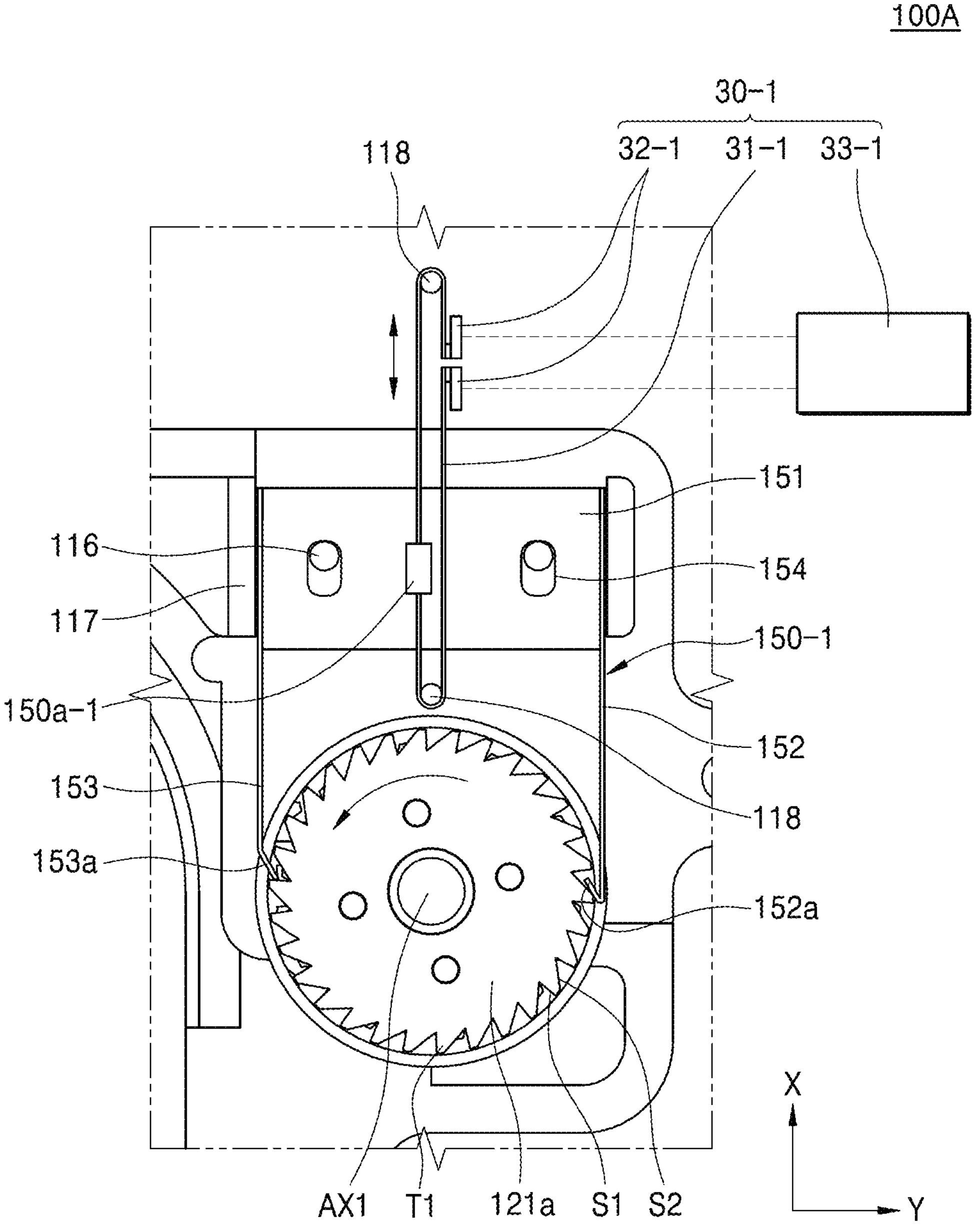
FIG. 8 is a diagram illustrating a drug discharge assembly according to another embodiment of the present disclosure.

FIG. 8 is a diagram illustrating a drug discharge assembly 100A according to another embodiment of the present disclosure.

Referring to FIG. 8, in the drug discharge assembly 100A, a drive module 30-1 may linearly move a drive piece 150-1.

The drive piece 150-1 is similar to the drive piece 150 of the above-described embodiment, and the drive piece 150-1 may include a body 151, a first arm 152, a second arm 153, and a guide hole 154. In addition, a first bent end 152*a* may be provided at an end of the first arm 152, and a second bent end 153*a* bent in a direction opposite to the first bent end may be provided at the end of the second arm 153.

The drive piece 150-1 may include a connector 150*a*-1 connected to the drive module 30-1. The connector 150*a*-1 is connected to a wire 31-1 of the drive module 30-1, and may be linearly moved in one direction according to the movement of the wire 31-1. The drive module 30-1 may transmit a driving force to the drive piece 150-1 to linearly reciprocate the drive piece 150-1. The drive module 30-1 may include the wire 31-1, a connection end 32-1, and a control unit 33-1.

The wire 31-1 is connected to the drive piece 150-1, and the drive piece 150-1 may be moved according to the contraction and elongation of the wire 31-1. The wire 150-1 may be contracted or extended in length according to a control signal applied from the control unit 33-1.

In one embodiment, the wire 31-1 may include a shape-memory alloy (SMA). The wire 31-1 may include a conventional shape-memory material and is not limited to a specific material. For example, the wire may include an alloy of nickel and titanium.

The connection end 32-1 is disposed at both ends of the wire 31-1, and receives electrical signals from the control unit 33-1. The connection end 32-1 may include an electrically conductive material.

The control unit 33-1 may generate and control a current signal. The control unit 33-1 may control a current applied to the connection end 32-1. The control unit 33-1 is connected to a battery (not illustrated) to control whether current is applied from the battery to the connection end 32-1.

For example, the control unit 33-1 may alternately apply an electrical signal to the connection end 32-1, whereby the wire 31-1 may linearly reciprocate along one direction. That is, when current is applied to only one of the connection ends 32-1, the drive piece 150-1 is advanced by contraction or extension of one end of the wire 31-1. In addition, when current is applied only to the other one of the connection ends 32-1, the drive piece 150-1 is retracted to its original position due to contraction or extension of the other end of the wire 31-1. As the control unit 33-1 controls the current signal applied to the connection end 32-1, the wire 31-1 is contracted or elongated, thereby allowing the drive piece to reciprocate in the front-rear direction.

Figure 9:
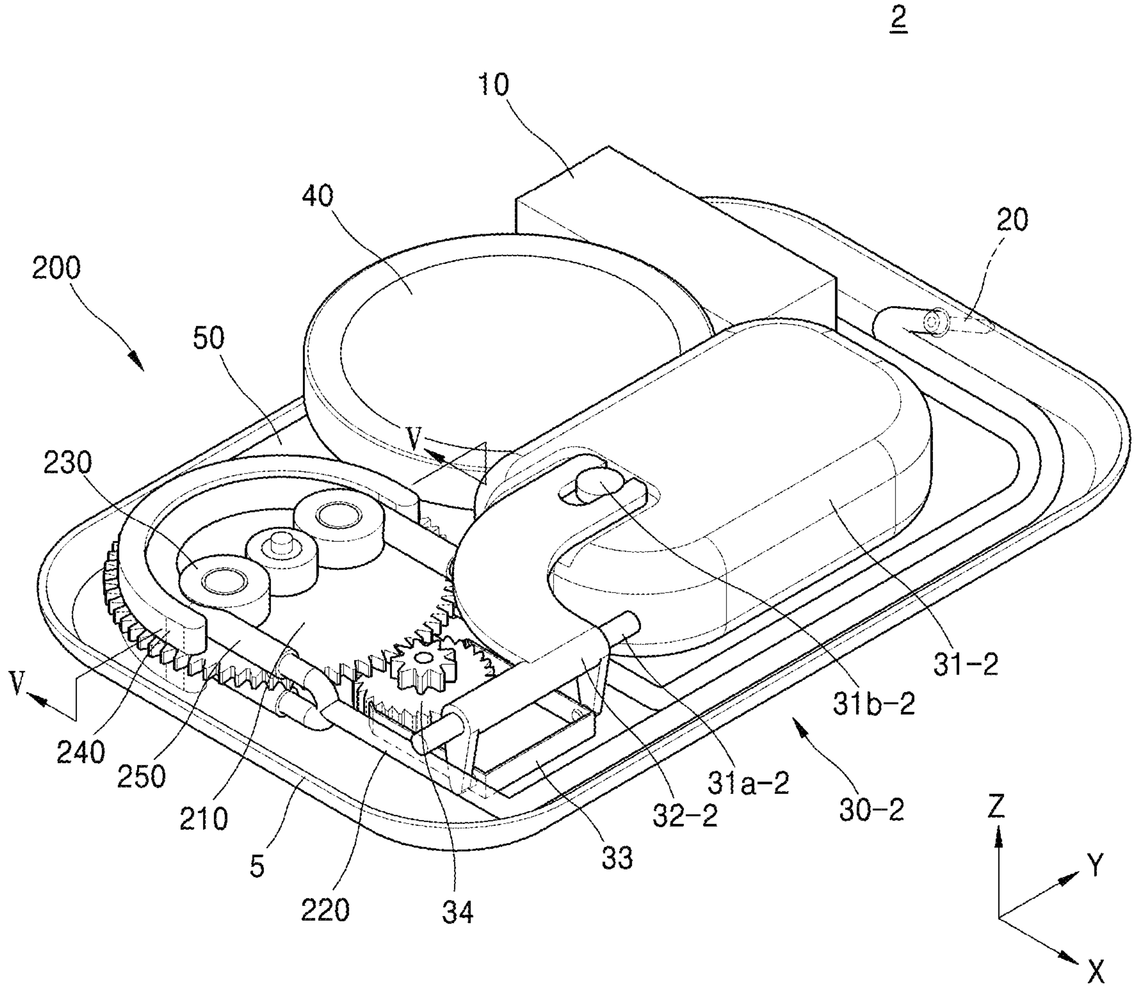
FIG. 9 is a perspective view illustrating a drug injection device according to another embodiment of the present disclosure.

FIG. 9 is a perspective view illustrating a drug injection device 2 according to another embodiment of the present disclosure.

Referring to FIG. 9, the drug injection device 2 may include a housing 5 covering the outside and an attachment 6 attached to a user's skin, and a plurality of parts are disposed in an inner space of the housing 5. The drug injection device 2 may include a reservoir 10, a needle assembly 20, a drive module 30-2, a battery 40, a controller 50, and a drug discharge assembly 200.

The reservoir 10 stores the drug to be injected, and is connected to the drug discharge assembly 200. The reservoir 10 may be mounted inside the housing 5. In another embodiment, the reservoir 10 may be provided outside the housing 5 as well. In addition, the reservoir 10 may further include a means for moving the drug, such as a pump (not illustrated).

The needle assembly 20 is disposed on one side of the housing 5. Since the needle assembly 20 is inserted into the user's skin, a drug to be discharged may be injected into the user. The drug discharge assembly 200 is provided between the needle assembly 20 and the reservoir 10, so that a drug may be distributed at a preset quantity or a preset period, and discharged through the needle assembly 20.

The drive module 30-2 may drive the drug discharge assembly 200. The drive module 30-2 may be connected to the drug discharge assembly 200 to transmit a driving force. The drive module 30-2 may include a body 31-2, a rotating piece 32-2, a drive piece 33, and a driving gear 34.

The body 31-2 is mounted inside the housing 5, and may rotate the rotating piece 32-2. The body 31-2 is electrically connected to the battery 40, receives a driving force, and rotates the rotating piece 32-2 with respect to a rotating shaft 31*a*-2.

The rotating piece 32-2 may be mounted on the body 31-2 and rotated, and the drive piece 33 connected to the rotating piece 32-2 may linearly reciprocate according to the rotation of the rotating piece 32-2. A part of the rotating piece 32-2 may be mounted on the protrusion 31*b*-2 of the body 31-2 and tilted. A part of the rotating piece 32-2 may be tilted in the left and right directions about the protrusion 31*b*-2. In addition, another part of the rotating piece 32-2 may be rotated by being inserted into the rotating shaft 31*a*-2 of the body 31-2. When a part of the rotating piece 32-2 is tilted, another part of the rotating piece 32-2 is rotated around the rotating shaft 31*a*-2, and the drive piece 33 may reciprocate along the teeth of the driving gear 34.

The drive piece 33 is inserted into the teeth of the driving gear 34 and may rotate the driving gear 34 in one direction during the linear reciprocation. The drive piece 33 is inserted into both sides of a first rotating gear 34*a* of the driving gear 34.

The drive piece 33 may include a first supporter 33*a* inserted into one side of the first rotating gear 34*a* and a second supporter 33*b* inserted into the other side. The first supporter 33*a* may have a first end 33*a*-1, and the second supporter 33*b* may have a second end 33*b*-1. The first end 33*a*-1 and the second end 33*b*-1 may be bent in different directions.

Figure 10:
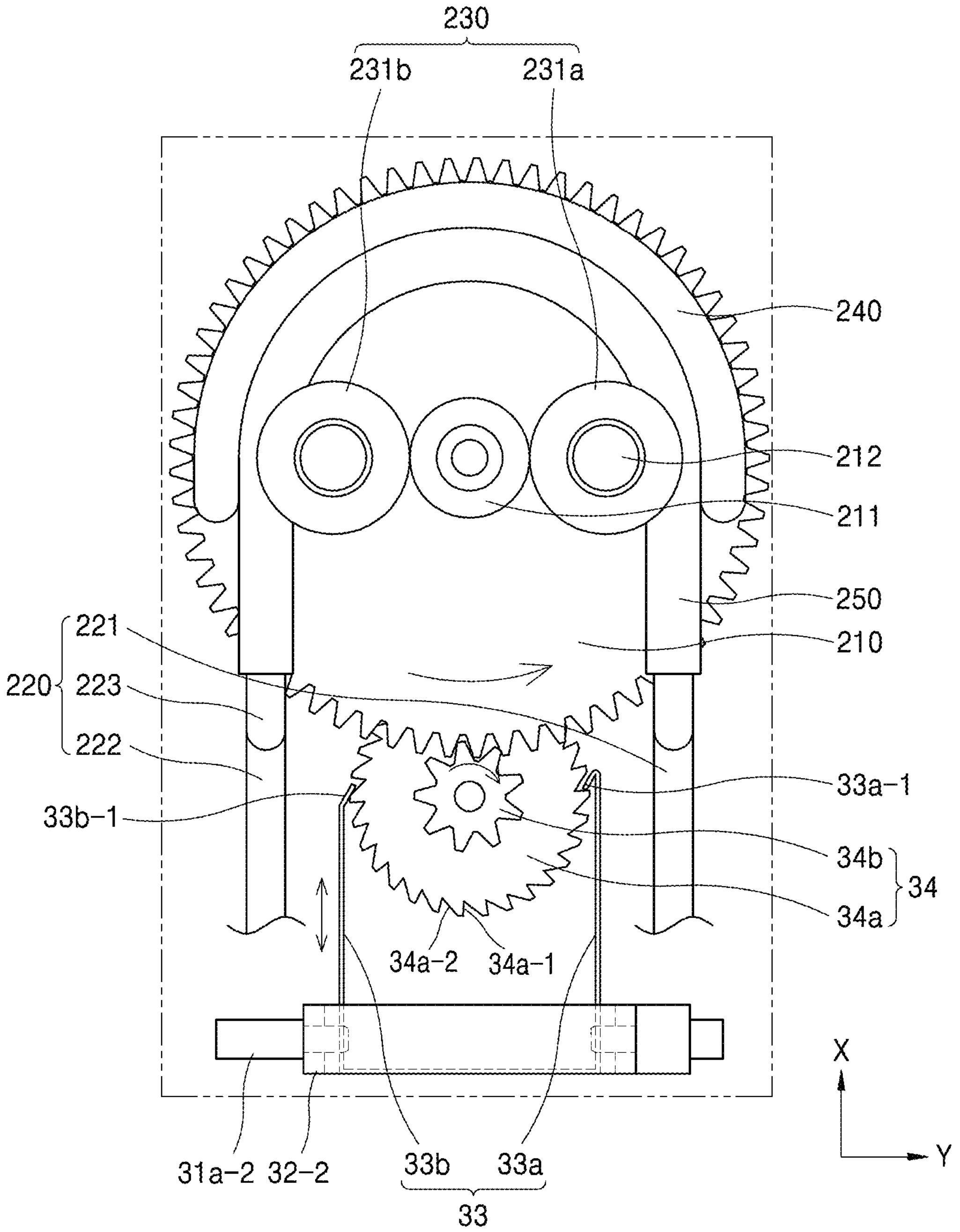
FIG. 10 is a plan view illustrating some parts of FIG. 9.

Referring to FIG. 10, the drive piece 33 may rotate the driving gear 34 in only one direction by the bending angle and direction of the first end 33*a*-1 and the second end 33*b*-1. The first end 33*a*-1 bent is formed at the end of the first supporter 33*a*. Since the first end 33*a*-1 is bent in a direction opposite to the first supporter 33*a*, it may support the teeth of the first rotating gear 34*a*. In detail, when the first supporter 33*a* is moved downward, the first end 33*a*-1 is moved downward while supporting a first wall 34*a*-1 of the teeth, so that the driving gear 34 may be rotated clockwise. In addition, when the first supporter 33*a* is moved upward, the first end 33*a*-1 is moved along a second wall 34*a*-2 of the teeth, so that a driving force is not transmitted to the driving gear 34.

The second end 33*b*-1 bent is formed at the end of the second supporter 33*b*, and since the second end 33*b*-1 is bent to have a slight inclination from the second supporter 33*b*, it moves along the teeth of the first rotating gear 34*a*, but may prevent rotation in the reverse direction. When the first end 33*a*-1 is moved downward, the second end 33*b*-1 is moved downward beyond the second wall 34*a*-2 of the teeth.

In addition, when the first supporter 33*a* is moved upward, the second end 33*b*-1 is moved upward while supporting the first wall 34*a*-1 of the teeth, so that the driving gear 34 may be rotated clockwise.

The driving gear 34 is engaged with a rotating member 210 of the drug discharge assembly 200. The driving gear 34 has the first rotating gear 34*a* connected to the drive piece 33 and a second rotating gear 34*b* engaged with the rotating member 210. A gear ratio between the first rotating gear 34*a* and the second rotating gear 34*b* may be determined according to an amount of drug to be discharged and a drug injection period.

The first supporter 33*a* and the second supporter 33*b* of the drive piece 33 may be inserted into the first rotating gear 34*a*. The drive piece 33 may be supported on both sides of the first rotating gear 34*a*. The teeth of the first rotating gear 34*a* are formed asymmetrically and may be rotated only in one direction. The first rotating gear 34*a* may include the first wall 34*a*-1 having a large slope and a short length, and the second wall 34*a*-2 having a small slope and a long length. When the drive piece 33 supports the first wall 34*a*-1, a driving force is transmitted, but the second wall 34*a*-2 is not supported and moves beyond the second wall 34*a*-2.

Since the first end 33*a*-1 of the first supporter 33*a* and the second end 33*b*-1 of the second supporter 33*b* are bent in different directions, the first end 33*a*-1 and the second end 33*b*-1 alternately transmit driving force. When the drive piece 33 is linearly moved downward, the first end 33*a*-1 rotates the driving gear 34 by supporting the first wall 34*a*-1, but the second end 33*b*-1 slides along the second wall 34*a*-2. When the drive piece 33 is linearly moved upward, the first end 33*a*-1 slides along the second wall 34*a*-2, but the second end 33*b*-1 rotates the driving gear 34 by supporting the first wall 34*a*-1. Therefore, when the drive piece 33 is linearly moved, the driving gear 34 may be continuously rotated in one direction.

The second rotating gear 34*b* is integrally formed with the first rotating gear 34*a*. When a driving force is transmitted to the first rotating gear 34*a*, the second rotating gear 34*b* may be rotated and rotate the rotating member 210. The battery 40 is electrically connected to the drive module 30-2 to transmit a driving force. The controller 50 may control driving of the drug injection device 2. The controller 50 may control driving of the drive module 30-2 to control a discharge period, a discharge amount, and a discharge speed of the drug.

The battery 40 is electrically connected to the drive module 30-2 to transmit a driving force. The controller 50 may control driving of the drug injection device 2. The controller 50 may control driving of the drive module 30-2 to control a discharge period, a discharge amount, and a discharge speed of the drug.

Figure 11:
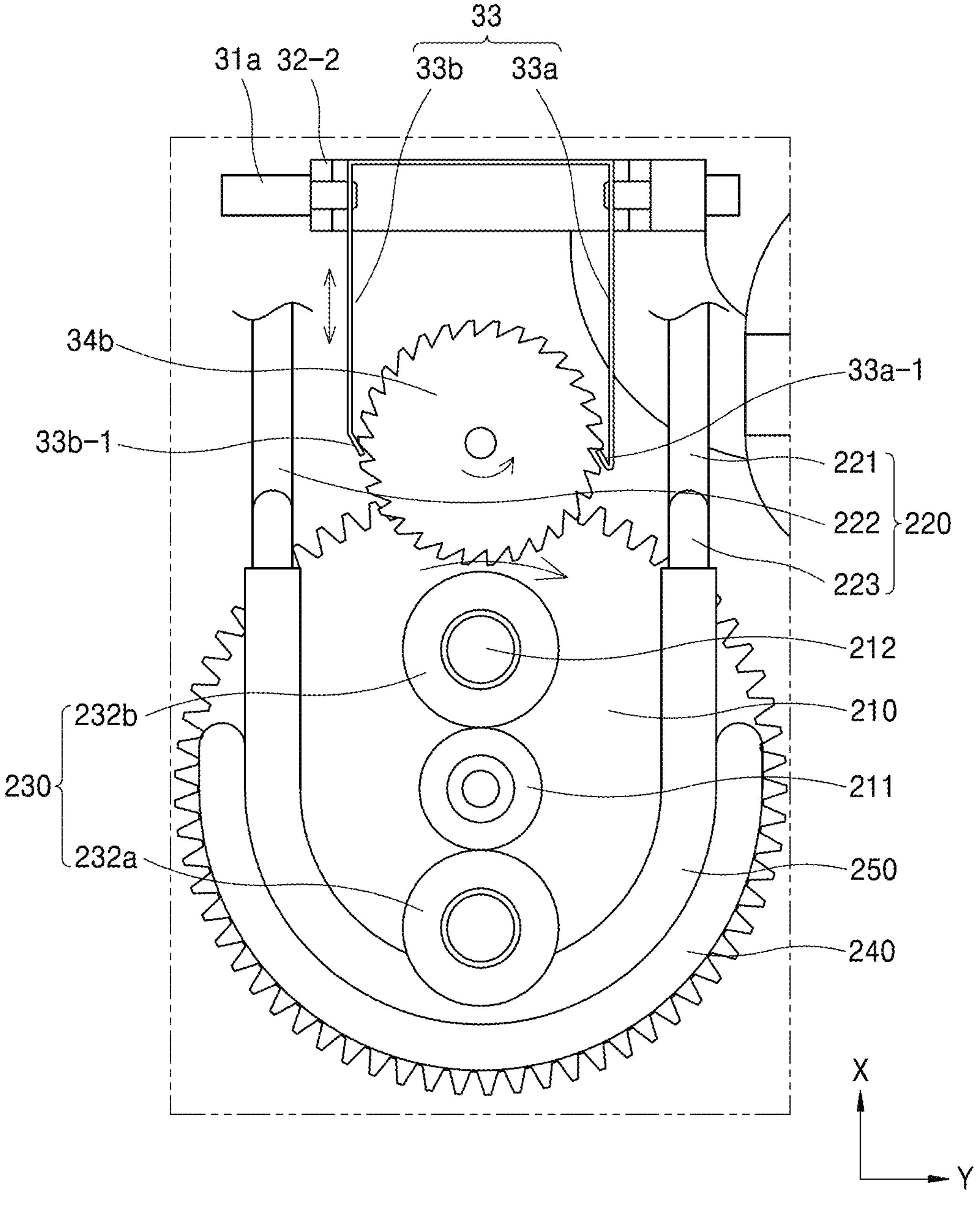
FIG. 11 is a bottom view illustrating some parts of FIG. 9.
Figure 12:
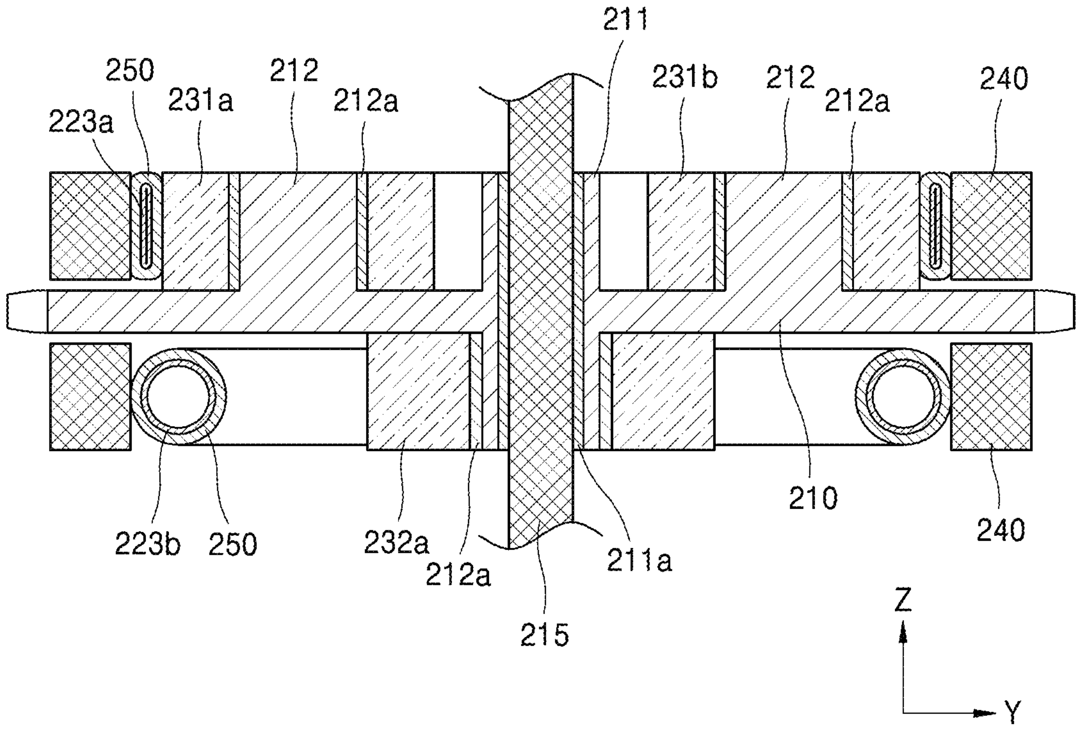
FIG. 12 is a cross-sectional view of a drug discharge assembly of FIG. 9.

FIG. 10 is a plan view illustrating some parts of FIG. 9, FIG. 11 is a bottom view illustrating some parts of FIG. 9, and FIG. 12 is a cross-sectional view of a drug discharge assembly 200 of FIG. 9.

Referring to FIGS. 10 to 12, the drug discharge assembly 200 may include the rotating member 210, a tube 220, a pressing unit 230, a guide portion 240, and a cover 250. The drug discharge assembly 200 compresses the tube 220 to quantitatively distribute the drug moving through the tube 220.

The rotating member 210 may be rotated in one direction. The rotating member 210 is engaged with the driving gear 34 and rotates in one direction by the driving gear 34 that rotates only in one direction. Referring to FIG. 10, since the driving gear 34 is rotated only in a clockwise direction, the rotating member 210 may be rotated only in a counterclockwise direction.

The rotating member 210 may be inserted into a supporting shaft 215 fixed to the housing 5 and rotate around the supporting shaft 215. The rotating member 210 may include a rib 211 protruding to surround the supporting shaft 215 and a plurality of fixed protrusions 212 supporting the pressing unit 230.

In an optional embodiment, a first bearing 211*a* may be provided between the supporting shaft 215 and the rotating member 210, and in another alternative embodiment, a second bearing 212*a* is provided between the fixed protrusion 212 and the pressing unit 230, so that the pressing unit 230 may be rotated.

The tube 220 may be provided between the reservoir 10 and the needle assembly 20, and may be provided to pass through the rotating member 210. Part of the tube 220 may extend in the circumferential direction of the rotating member 210. The tube 220 may include a flexible material. Accordingly, when the pressing unit 230 is in close contact therewith, the tube 220 may be compressed.

The tube 220 may include an inlet end 221 introduced from the reservoir 10 and an outlet end 222 discharged to the needle assembly 20. In addition, a curved portion 223 is formed between the inlet end 221 and the outlet end 222, and the curved portion 223 may extend along the circumferential direction of the rotating member 210. Since the curved portion 223 is disposed to be spaced apart from the surface of the rotating member 210, even if the rotating member 210 is rotated, it is fixed to a preset position.

The curved portion 223 is branched from the inlet end 221 to the outlet end 222, and the branched curved portion 223 extends in the circumferential direction parallel to each other. The curved portion 223 may extend to both surfaces of the rotating member 210. A first curved tube 223*a* may be disposed in a circumferential direction along one surface of the rotating member 210, and a second curved tube 223*b* may be disposed in a circumferential direction along the other surface of the rotating member 210.

Since the tube 220 extends to both surfaces of the rotating member 210, the drug may be continuously and precisely discharged. In the case where the tube extends in the form of only one tube, since the period of precisely controlling and discharging the drug is determined by the rotation period of the rotating member 210, the rotational speed of the rotating member needs to be increased in order to discharge a large amount of drug. However, when the rotational speed of the rotating member is excessively high, stability and durability are deteriorated due to overload and heat generation of the driving unit.

Since the tube 220 according to an embodiment of the present disclosure extends to both sides of the rotating member 210, the discharge period of the drug may be shortened, so the overload of the drive module 30-2 is reduced, and durability and stability may be improved. In addition, since the first curved tube 223*a* and the second curved tube 223*b* have different discharge periods, the amount of drug may be precisely controlled.

In another embodiment, the first curved tube 223*a* and the second curved tube 223*b* may have diameters smaller than that of the inlet end 221 or the outlet end 222. Since the diameters of the first curved tube 223*a* and the second curved tube 223*b* are formed to be small, the discharge amount of the drug may be precisely controlled.

The pressing unit 230 may be mounted on the rotating member 210, and press the tube 220 when the rotating member 210 rotates. The pressing unit 230 may have a plurality of rollers spaced apart at preset intervals along the circumferential direction of the rotating member 210.

The pressing unit 230 may be inserted into the fixed protrusion 212 of the rotating member 210 and rotated around the fixed protrusion 212. That is, the pressing unit 230 may rotate around the fixed protrusion 212 of the rotating member 210 and orbit around the supporting shaft 215 by the rotation of the rotating member 210. Since the pressing unit 230 rotates, friction with the tube 220 is reduced, and the tube 220 may be gently compressed. Since the pressing unit 230 orbits, the pressing unit 230 may periodically and quantitatively discharge drug.

The pressing unit 230 may be mounted on both surfaces of the rotating member 210. A first roller unit 231 is mounted on one surface of the rotating member 210 and may press the first curved tube 223*a*. A second roller unit 232 is mounted on the other surface of the rotating member 210 and may press the second curved tube 223*b*. first roller unit 231 and the second roller unit 232 may be arranged to be offset from each other.

The first roller unit 231 includes a first-a roller 231*a* and a first-b roller 231*b* disposed at 180 degree intervals from each other, and the second roller unit 232 may include a second-a roller 232*a* and a second-b roller 232*b* disposed at 180 degree intervals from each other. The number of the first roller 131 and the number of the second roller 132 are not limited thereto, and may be variously set according to a discharge period and a discharge amount of the drug.

In detail, referring to FIG. 5, the second-a roller 232*a* is disposed between the first-a roller 231*a* and the first-b roller 231*b*. Both sides of the first curved tube 223*a* are compressed by the first roller unit 231, but the second curved tube 223*b* is compressed by the second roller unit 232 in the middle of the first roller unit 231. The first roller unit 231 and the second roller unit 232 may press the tube 220 at different periods.

Since the first roller unit 231 and the second roller unit 232 have different rotation periods, drugs are alternately discharged from the first curved tube 223*a* and the second curved tube 223*b*. As a result, since the drug is discharged in a short period, the drug discharge assembly 200 may inject drug quickly and accurately.

The guide portion 240 may extend along the circumferential direction of the rotating member 210 and support the tube 220. Since the guide portion 240 extends along the curved portion 223 and supports one side of the tube 220, when the first roller unit 231 or the second roller unit 232 is rotated, the tube 220 may be compressed.

The drawing illustrates an embodiment in which the guide portion 240 is disposed outside the tube 220 and the pressing unit 230 is disposed inside the tube 220, but is not limited thereto, in another embodiment, the guide portion may be disposed inside of the tube and the pressing portion may be disposed outside of the tube.

Since the guide portion 240 is fixed to the housing 5, the guide portion 240 may align the position of the tube 220. Since the guide portion 240 is spaced apart from the rotating member 210 at a certain interval, the position may be fixed even when the rotating member 210 rotates.

The cover 250 may be provided to surround the tube 220 pressed by the pressing unit 230. The cover 250 may be provided to cover the curved portion 223, and may include a flexible material. The cover 250 may prevent the curved portion 223 from being damaged by the pressing unit 230. Since the cover 250 is in contact with the pressing unit 230 on the outer circumferential surface of the curved portion 223, it is possible to prevent damage to the curved portion 223 by the pressing unit 230 by dispersing the force transmitted from the pressing unit 230.

Since the curved portion 223 of the tube 220 extends in the circumferential direction while having a curvature, it may be easily damaged by an external force. Since the cover 250 covers the tube 220, durability of the tube 220 may be increased.

Figure 13:
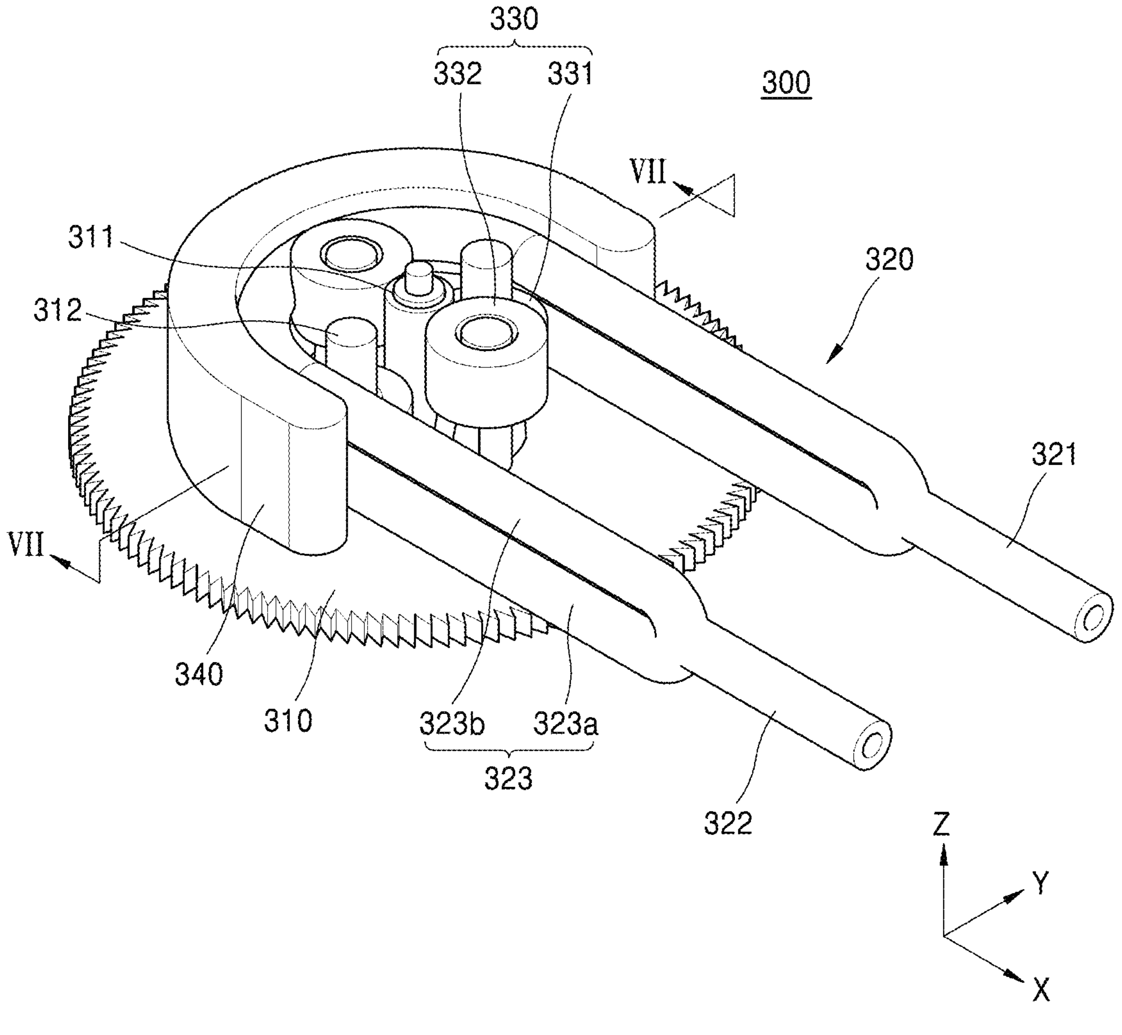
FIG. 13 is a perspective view illustrating a drug discharge assembly according to another embodiment of the present disclosure.
Figure 14:
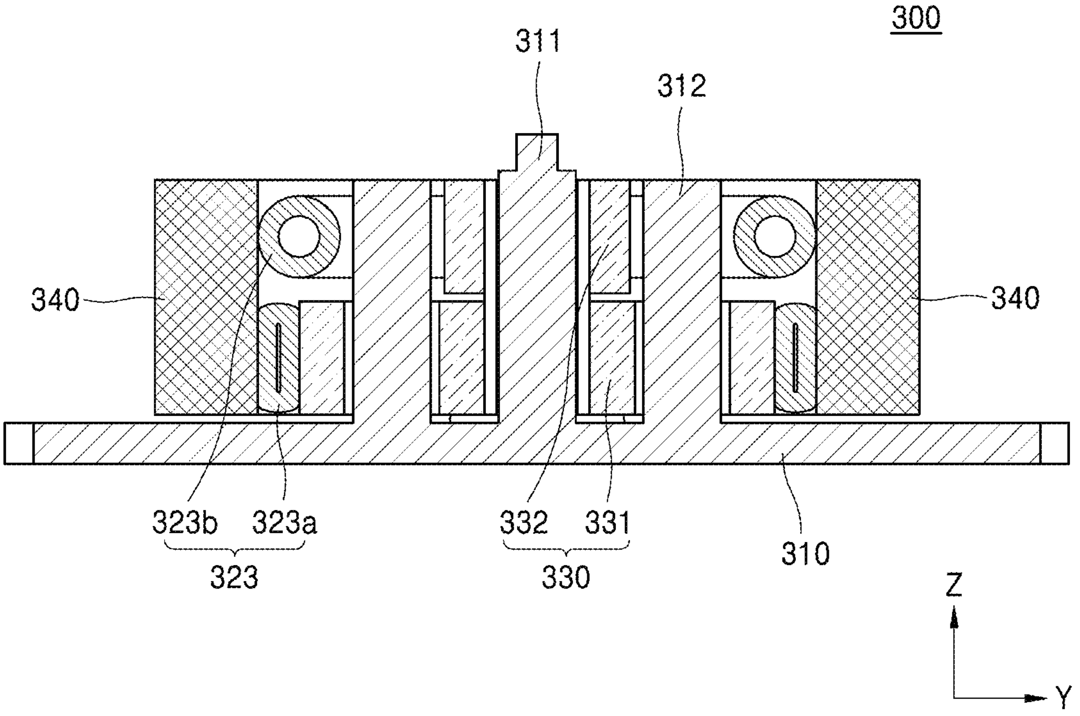
FIG. 14 is a cross-sectional view taken along VII-VII of FIG. 13.

FIG. 13 is a perspective view illustrating a drug discharge assembly 300 according to another embodiment of the present disclosure, and FIG. 14 is a cross-sectional view taken along VII-VII of FIG. 13.

Referring to FIGS. 13 and 14, a drug discharge assembly 300 may include a rotating member 310, a tube 320, a pressing portion 330 and a guide portion 340.

The tube 320, the pressing portion 330 and the guide portion 340 may be provided on one surface of the rotating member 310. The rotating member 310 may be rotated around a supporting shaft 311. The rotating member 310 may include a fixed protrusion 312 into which the pressing portion 330 is inserted.

The tube 320 has a curved portion 323 disposed between an inlet end 321 and an outlet end 322. The curved portion 323 extends at different heights on one surface of the rotating member 310. A first curved tube 323*a* and a second curved tube 323*b* are branched at the inlet end 321 and joined at the outlet end 322, and are arranged to be parallel to the height direction on one surface of the rotating member 310.

The pressing portion 330 may include a first roller 331 and a second roller 332 disposed on one surface of the rotating member 310. The first roller 331 may press the first curved tube 323*a*, and the second roller 332 may press the second curved tube 323*b*.

Since the first roller 331 and the second roller 332 are arranged to deviate from each other, the first curved tube 323*a* and the second curved tube 323*b* may have different discharge periods. In the drug discharge assembly 300, since the first curved tube 323*a* and the second curved tube 323*b* discharge drug at different periods, the drug may be rapidly and accurately injected into the patient.

A drug discharge assembly and a drug injection device according to an embodiment of the present disclosure may quantitatively inject drug. Since the tube is branched from the rotating member, a plurality of passages for moving and distributing drug may be formed, and the pressing portion may precisely and quantitatively distribute the drug.

A drug discharge assembly and a drug injection device according to an embodiment of the present disclosure may rapidly inject drug. Since a branched tube has different discharge cycles, the drug discharge assembly may quickly discharge drug.

A drug discharge assembly and a drug injection device according to an embodiment of the present disclosure may improve durability. Since the drug discharge assembly has a cover surrounding a tube, durability of the tube having a predetermined curvature may be improved.

The spirit of the present disclosure should not be limited to the above-described embodiments, in addition to the claims to be described later, all ranges equivalent to or equivalently changed from the claims fall within the scope of the spirit of the present disclosure.

According to an embodiment of the present disclosure, a drug discharge assembly and a drug injection device may be applied to various industrially available devices. The drug discharge assembly and the drug injection device may be applied to a device for delivering various drugs.

What is claimed is:

1. A drug discharge assembly comprising:

a drive piece configured to be linearly reciprocated along one direction;

a rotating unit in contact with an end of the drive piece and configured to rotate in one direction according to a linear reciprocating motion of the drive piece;

a flexible tube disposed adjacent to the rotating unit and having a curved section at least partially extending in a circumferential direction; and a pressing unit mounted on the rotating unit and configured to rotate while pressing the flexible tube according to a rotation of the rotating unit, wherein the drive piece comprises:

a body;

a first arm extending from the body and having a first bent end bent at a preset angle with respect to a length direction at an end thereof; and a second arm extending from the body and having a second bent end bent in a direction different from that of the first bent end at an end thereof, a portion of the second arm disposed in parallel with a portion of the first arm, wherein the first bent end presses a tooth of teeth of the rotating unit when the drive piece moves backward, wherein the second bent end presses another tooth of the teeth of the rotating unit when the drive piece moves forward, wherein the rotating unit comprises:

a first rotating member including:

a first rotating gear provided with a plurality of first teeth and disposed to contact at least one of a first arm and a second arm of the drive piece, the first rotating gear being rotatable about a first axis by receiving a driving force from the drive piece; and a second rotating gear integrally formed with the first rotating gear and provided with a plurality of second teeth, the second rotating gear configured to rotate together with the first rotating gear about the first axis; and a second rotating member having a plate shape and rotatable about a second axis, the second rotating member being connected to the second rotating gear and including a plurality of third teeth engaged with the second teeth, the second rotating member being configured to rotate in accordance with the rotation of the second rotating gear, and wherein an amount of drug discharged per one actuation of the drive piece is determined by one or both of a ratio of a number of the first teeth and a number of the second teeth and a ratio of the number the second teeth and a number of the third teeth.

2. The drug discharge assembly of claim 1, wherein the pressing unit is configured to press the flexible tube when the pressing unit contacts the curved section of the flexible tube so that the flexible tube is compressed at a contact point.

3. A drug injection device comprising:

a needle assembly;

a reservoir configured to store a drug discharged to the needle assembly;

a drive module configured to linearly reciprocate a drive shaft;

a drive piece connected to the drive shaft and configured to be linearly reciprocated according to a movement of the drive shaft;

a rotating unit in contact with an end of the drive piece and configured to rotate in one direction according to a linear reciprocating motion of the drive piece;

a flexible tube disposed between the needle assembly and the reservoir and having a curved section at least partially extending in a circumferential direction; and a pressing unit mounted on the rotating unit and configured to rotate while pressing the flexible tube according to a rotation of the rotating unit, wherein the drive piece comprises:

a body;

a first arm extending from the body and having a first bent end bent at a preset angle with respect to a length direction at an end thereof; and a second arm extending from the body and having a second bent end bent in a direction different from that of the first bent end at an end thereof, a portion of the second arm disposed in parallel with a portion of the first arm, wherein the first bent end presses a tooth of teeth of the rotating unit when the drive piece moves backward, and wherein the second bent end presses another tooth of the teeth of the rotating unit when the drive piece moves forward, wherein the rotating unit comprises:

a first rotating member including:

a first rotating gear provided with a plurality of first teeth and disposed to contact at least one of a first arm and a second arm of the drive piece, the first rotating gear being rotatable about a first axis by receiving a driving force from the drive piece; and a second rotating gear integrally formed with the first rotating gear and provided with a plurality of second teeth, the second rotating gear configured to rotate together with the first rotating gear about the first axis; and a second rotating member having a plate shape and rotatable about a second axis, the second rotating member being connected to the second rotating gear and including a plurality of third teeth engaged with the second teeth, the second rotating member being configured to rotate in accordance with the rotation of the second rotating gear, and wherein an amount of drug discharged per one actuation of the drive piece is determined by one or both of a ratio of a number of the first teeth and a number of the second teeth and a ratio of the number the second teeth and a number of the third teeth.

* * * * *